(12) United States Patent
Binz et al.

(10) Patent No.: US 8,762,624 B2
(45) Date of Patent: Jun. 24, 2014

(54) DATA MANAGEMENT SYSTEM AND METHOD USING NONVOLATILE AND VOLATILE MEMORIES AND LINKED LISTS TO SEQUENTIALLY STORE DATA RECORDS OF DIFFERENT CATEGORY TYPES

(75) Inventors: Joachim Binz, Mainaschaff (DE); Manfred Ebner, Oberursel (DE); Mario Esser, Griesheim (DE); Stephan Muller-Pathle, Darmstadt (DE); Thomas Jetter, Mainz (DE)

(73) Assignee: Lifescan Scotland Limited, Inverness (GB)

( * ) Notice: Subject to any disclaimer, the term of this patent is extended or adjusted under 35 U.S.C. 154(b) by 238 days.

(21) Appl. No.: 12/674,760

(22) PCT Filed: Aug. 29, 2007

(86) PCT No.: PCT/EP2007/007558
§ 371 (c)(1),
(2), (4) Date: Feb. 23, 2010

(87) PCT Pub. No.: WO2009/026946
PCT Pub. Date: Mar. 5, 2009

(65) Prior Publication Data
US 2011/0099338 A1    Apr. 28, 2011

(51) Int. Cl.
*G06F 12/00* (2006.01)
*G06F 17/40* (2006.01)
*G06F 19/00* (2011.01)
*A61B 5/00* (2006.01)

(52) U.S. Cl.
USPC ............................ 711/103; 702/187; 600/365

(58) Field of Classification Search
USPC ....................................................... 711/103
See application file for complete search history.

(56) References Cited

U.S. PATENT DOCUMENTS 5,682,497 A * 10/1997 Robinson ...................... 711/103
5,708,247 A    1/1998 McAleer et al. ......... 204/403.05

(Continued)

FOREIGN PATENT DOCUMENTS

DE    10128752 A1    12/2002
EP      1031929 A3     8/2000

(Continued)

OTHER PUBLICATIONS

Dai, H., et al: "ELF: An efficient log-structured flash file system for micro sensor nodes" Proc. Second Int. Conf. Embedded Networked Sensor Syst.: Sensys '04—Proceedings of the Second International Conference on Embedded Networked Sensor Systems; Sensys '04—Proceedings of the second International Conference on Embedded Networked Sensor, 2004 pp. 176-187, XP002479775.

(Continued)

*Primary Examiner* — Sanjiv Shah
*Assistant Examiner* — Glenn Gossage

(57) ABSTRACT

A data management system and method for storing data records of at least two different category types in a first non-volatile memory section, which may be flash memory, divided into sequentially arranged memory locations. The data records, each including its category type and a time stamp, are sequentially stored into memory locations indicated by a cyclic write pointer stored in a second nonvolatile memory section. A new node associated with a data record is added to a linked list stored in a volatile memory section for a determined category type, such that there is a separate linked list for each category type. The data management system may be included in a glucose meter of a blood glucose system, and use of the second nonvolatile memory section and the volatile memory sections allows data records stored in the first nonvolatile memory section to be displayed by category type and by time stamp more quickly.

39 Claims, 6 Drawing Sheets

(56) References Cited

U.S. PATENT DOCUMENTS

| | | | |
|---|---|---|---|
| 6,046,051 A | 4/2000 | Jina | 436/69 |
| 6,301,635 B2 * | 10/2001 | Bothwell et al. | 711/103 |
| 6,412,080 B1 | 6/2002 | Fleming et al. | 711/103 |
| 6,535,949 B1 * | 3/2003 | Parker | 711/103 |
| 6,542,910 B2 | 4/2003 | Cork et al. | 707/999.205 |
| 6,733,655 B1 | 5/2004 | Davies et al. | 205/775 |
| 6,865,658 B2 | 3/2005 | Tomori et al. | 711/173 |
| 2003/0046482 A1 | 3/2003 | Venkiteswaran | 711/103 |
| 2003/0200232 A1 | 10/2003 | Matsuoka et al. | 707/999.2 |
| 2005/0055496 A1 | 3/2005 | Nallapa | 711/103 |
| 2006/0036802 A1 * | 2/2006 | Drukin | 711/103 |
| 2007/0033332 A1 * | 2/2007 | Sinclair et al. | 711/103 |

FOREIGN PATENT DOCUMENTS

| | | |
|---|---|---|
| WO | WO 01/67099 A1 | 9/2001 |
| WO | WO 01/73124 A3 | 10/2001 |

OTHER PUBLICATIONS

Woodhouse, D., "JFFS: The Journalling Flash Filed System" Internet Citation, [online] XP007901740, retraived from the Internet: URL: http://sources.redhat.com/jffs2/jffs2.pdf [retrieved on Feb. 15, 2007].

* cited by examiner

| Address | Category Type | Data Record | Time Stamp |
|---|---|---|---|
| 0x40000 | EBGM | 60 | 1-Jan-2005 Mon 0600 |
| 0x40010 | EBGM | 75 | 1-Jan-2005 Mon 0800 |
| 0x40020 | EBGM | 300 | 1-Jan-2005 Mon 0900 |
| 0x40030 | P.Basal | 1 | 1-Jan-2005 Mon 0901 |
| 0x40040 | EBGM | 85 | 1-Jan-2005 Mon 1000 |
| 0x40050 | P.Basal | 0.75 | 1-Jan-2005 Mon 1005 |
| 0x40060 | EBGM | 100 | 1-Jan-2005 Mon 1100 |
| 0x40070 | | | |
| 0x40080 | | | |

*FIG. 6*

DATA MANAGEMENT SYSTEM AND METHOD USING NONVOLATILE AND VOLATILE MEMORIES AND LINKED LISTS TO SEQUENTIALLY STORE DATA RECORDS OF DIFFERENT CATEGORY TYPES

PRIORITY

This application claims the benefits of priority under 35 USC §§ 120, 363, and 365 from International Application No. PCT/EP2007/007558 filed Aug. 29, 2007, which is incorporated herein by reference in its entirety.

The present invention relates to A data management system and method for storing a plurality of data records in a non-volatile memory section.

In many areas of technology, systems are utilized that include one or more devices that periodically or continuously generate data during their operation, such as e.g. data relating to operational conditions of the devices or data relating to various measurements of physical values performed by the devices. Often, it is desirable or necessary to centrally store such data in a non-volatile manner, so that later-on a history of the operation of the respective system can be retrieved e.g. in the form of one or more reports. For this purpose, the data are stored together with an indication of their chronological relationship enabling their retrieval in a chronological order. In many systems of this kind, data of more than one category type are generated, such as e.g. various different operational parameters and/or various different sensed or measured parameters, for example sensed flow rates, concentrations or pressures. Generally, the data have to be stored so that separate reports can be generated for the different category types.

One example of such systems are blood glucose systems utilized for diabetes therapy and relieving a diabetes patient of the daily use of syringes or insulin pens. Blood glucose systems usually comprise a battery-operated blood glucose meter including a control unit and one or more separate further peripheral medical devices, such as, for example, a battery-operated insulin pump. In operation, the blood glucose meter is used to determine the blood glucose concentration, e.g. by receiving blood samples via enzyme-based test strips and calculating the blood glucose value based on the enzymatic reaction. Advantageously, the blood glucose system is configured such that the measured value is automatically delivered to the control unit. The insulin pump allows for the delivery of insulin in a physiological manner and can be controlled to follow standard or individually modified protocols to give the patient a better glycemic control over the course of a day as compared to manual therapy. It can be constructed as an implantable device for subcutaneous arrangement or can be constructed as an external device that is carried on the body of the patient.

The operation of the insulin pump and of other devices can be controlled and modified by means of the control unit. For example, delivery of suitable amounts of insulin by the insulin pump requires that the patient frequently determines his or her blood glucose level and that this value is provided to the control unit, which then calculates a suitable modification to the default or currently in use insulin delivery protocol, i.e. dosage and timing, and subsequently communicates with the insulin pump to adjust its operation accordingly. In this regard, it may be necessary to use the control unit each time the patient eats to instruct the pump to administer a specified amount of insulin to cover that meal. Recently, a more or less closed-loop control has been realized in which the control unit modifies the insulin delivery protocol automatically.

In view of the permanence of the therapy and in view of the fact that the patient is not under permanent medical observation, the need exists to store operational and functional data allowing monitoring of the operation of the blood glucose system and of the effect of the insulin delivery protocol provided by the system. Therefore, the glucose meter is typically adapted to persistently store data generated by the meter itself or the peripheral medical devices and having different category types such as, for example, an episodic glucose measurement, a comment about the episodic glucose measurement, an insulin bolus amount, an insulin bolus rate and/or an amount of insulin remaining in the pump reservoir, in a non-volatile memory. For example, by periodically storing insulin pump data and glucose concentration data for various points in time, it is advantageously possible to conduct a contemporaneous comparison between the effects of insulin therapy on the resulting glucose concentration and to thereby verify the effectiveness of the current system settings.

Thus, various systems are known in the medical field as well as in other fields of technology, in which system data of various types are stored in a non-volatile memory together with an indication of a chronological order. One exemplary system of this kind is the blood processing system described in U.S. Pat. No. 6,542,910. This reference discloses a blood processing system that is adapted to store status data about the operational and functional conditions of the processing procedure, wherein the status data may include fluid flow rates, sensed pressures and fluid volumes measured. These data are periodically generated as time stamped data and are stored in their chronological order in a flash memory. In the flash memory, distinct storage areas of predetermined size are reserved, each of which is used to store data of only one type, such as event data or system condition data. Some of the storage areas may be utilized to form a ringfile in which the oldest data is always overwritten once the storage area is full.

While this prior art system provides for the persistent storage of various types of data together with the possibility to generate reports, it has several disadvantages. For example, since the frequency cannot be foreseen with which the various types of data are generated, the situation regularly occurs that the storage area for a particular category type is full and old data have to be overwritten, while other storage areas are not yet full. Thus, data are lost although there is still memory capacity left. Furthermore, it is not possible to add storage capability for new category types of data.

Flash memory is one type of non-volatile memory—i.e. memory that, as opposed to volatile memory, does not need power to maintain the information stored therein—that is regularly used for persistent data storage in systems of the above kind. However, when using flash memory, the specific characteristics of this memory type have to be taken into consideration. Flash memory has the limitations that bit level modifications are only possible in one direction from an erased state into a programmed state (i.e. from "0" to "1" or from "1" to "0", but not both), and that each erasing operation always erases a relatively large area comprising a plurality of bytes. Thus, while writing and reading of individual bits and bytes of data is possible in a random access manner, writing of data to a particular area of the flash memory generally requires that this area is in its erased state, i.e. that an erase operation was performed that did not only erase the area required to store the data, but also adjacent areas.

It is an object of the present invention to provide a system and a method for storing data of various category types in a non-volatile memory that provide an optimized usage of nonvolatile memory and provide flexibility with regard to the category types, and that remedy the disadvantages found in the prior art.

This object is achieved by a data management system and method in accordance with the preferred embodiments of the claimed invention.

The data management system of the present invention comprises a first non-volatile memory section that is divided into a plurality of sequentially arranged, preferably equally sized memory locations. Each of these memory locations is identified by an address by means of which it can be accessed. The address may be a physical address or a logical address, such as an index of the memory location within the section. The plurality of memory locations includes a first memory location at one end of the first non-volatile memory section and a last memory location at the opposite end thereof.

The data management system further comprises a volatile memory section and a storage controller that is operably connected to the first non-volatile memory section and the volatile memory section. The storage controller, which may comprise or be provided in the form of a suitably programmed microprocessor, is adapted to receive a plurality of data records including data records of at least two different category types, wherein each data record comprises a data value, an indication of the category type of the data record, and a time stamp including time information.

These data records may be generated by one or more devices or be generated based on data provided by one or more devices and may constitute operational and/or functional data of an overall system of which the data management system is a part. Such operational data and functional data may e.g. be data corresponding to measurements of physical conditions characterizing the state of system components or a process carried out by the overall system. For example, some data records may indicate the fill level of a liquid stored in a particular device, such as e.g. the fill level of insulin within an insulin pump, or the concentration of a particular substance in a process liquid, such as e.g. the glucose concentration in the blood of a patient. The time stamp indicates a date and time associated with each data record, and may e.g. indicate the date and time at which a measurement was performed. The category type indicates the type of data value included in the data record, e.g. fill level of a liquid in device A, fill level of a liquid in device B, concentration measured by device C and concentration measured by device D.

The storage controller is further adapted to determine the category type of each received data record on the basis of the indication of the category type of the respective data record, and to sequentially store one by one the data records in the order they are received, regardless of their category type in the first non-volatile memory section by storing each data record into a memory location indicated by a write pointer that is maintained by the storage controller and that is incremented after each storage of a data record. In this context, incrementing means that after storing of a data record the write pointer is manipulated to indicate, in the direction from the first memory location towards the last memory location, the next memory location or, in case the last data record was stored into the last memory location, the first memory location. In other words, with respect to the writing operation, the storage controller is adapted to use the first non-volatile memory section in the manner of a circular buffer. The write pointer may be provided in the form of a storage area in a memory, in which storage area the address or a value characteristic of the address of a memory location of the first non-volatile memory section is stored, wherein in operation the address or value is updated by the storage controller following storing of any data record.

In this manner, each memory location storing a data record stores exactly one data record, and in case the plurality of data records are stored without intermediate editing or deleting of data records described later on and without reaching the end of the first non-volatile memory section, the data records are stored in the order they are received and without regard to their category type and their time stamp in successive memory locations of the first non-volatile memory section.

The storage controller is further adapted to add for each received data record a new node associated with the respective data record to a linked list that is stored in the volatile memory section for the determined category type of the respective data record, such that following storing all received data records there is a separate linked list stored in the volatile memory section for each category type included in the plurality of data records, and such that for each such linked list the nodes are only associated with data records of the same category type and the sequence of the nodes is such that the associated data records are temporally sorted according to their time stamp. Each node constitutes an information set pertaining to a particular data record stored in the first non-volatile memory section. All nodes of a particular linked list are associated with data records of a common category type, and, in the preferred case of a doubly linked list, comprise a pointer to the previous and subsequent node, i.e. an index or address of the respective node within the volatile memory section.

This data management system provides the advantage that it is easily possible to store data records of different category types in every kind of non-volatile memory, while ensuring that data records are only overwritten if the entire first non-volatile memory section is occupied (i.e. the maximum number of data records can be stored independent of record type) and that separate, chronological reports for each category type can be easily generated. By using the linked list for a category type of interest, the data records of this category type can be selectively retrieved from the first non-volatile memory section sorted according to their time stamp. Since the number of nodes of each of the different linked lists is generally much smaller than the number of data records stored in the first non-volatile memory section, insertion of a node into a linked list is possible rapidly. The data management system is particularly advantageous in systems, in which devices deliver the data records type by type and not in overall chronological order, so that the records in flash are not chronologically sorted, but the records of a particular type are chronologically sorted.

In addition, the system is able to handle data having new and unknown category types by automatically generating a new linked list for each new category type. For example, the storage controller may be adapted to determine for each data record to be stored in the first non-volatile memory section whether there is already a linked list stored in the volatile memory section for the determined category type of the respective data record, and if there is no such linked list to allocate a fresh linked list and to add the new node associated with the respective data record to the fresh linked list.

For a particularly effective use of the volatile memory section, the volatile memory section may comprise a plurality of sequentially arranged memory locations, each linked by a predetermined relationship stored in the storage controller to exactly one memory location of the first non-volatile memory section, and the storage controller may be adapted to effect adding a new node to a linked list by storing the node in the memory location of the volatile memory section that is linked by the predetermined relationship to the memory location of the first non-volatile memory section in which the data record associated with the respective node is stored. In other words, the nodes or information sets do not include an indication of a memory location of the first non-volatile memory section, which indication is stored as a value within the node or information set, but the relative storage positions of the nodes or information sets within the volatile memory section provide such indications. In this manner, the linked lists within the volatile memory section physically intersect each other, but are logically distinct, and no memory locations of the volatile memory section are occupied by nodes not associated with currently stored data records.

To provide the possibility of deleting data records, the storage controller may further be adapted to receive an input signal indicating that a data record stored in the first non-volatile memory section is to be deleted, and to delete the data record from the first non-volatile memory section by manipulating at least one bit within the memory location of the first non-volatile memory section in which memory location the data record is stored in order to indicate that the memory location does not include a valid data record, and by removing the node associated with the data record from the corresponding linked list stored in the volatile memory section. Thus, the data records are not immediately physically deleted and may still be read from the raw non-volatile memory contents, e.g. the raw flash memory contents. However, there is no longer a node of a linked list associated with the deleted data record, so that it is e.g. no longer considered when generating reports by means of the linked lists.

Similarly, to provide the possibility of changing data records, the storage controller may further be adapted to receive an input signal indicating that and in which manner a data record stored in the first non-volatile memory section is to be changed, and to store the changed version of the data record in the memory location of the first non-volatile memory section currently indicated by the write pointer, manipulate at least one bit within the memory location of the first non-volatile memory section in which memory location the original version of the data record is stored in order to indicate that the memory location does not include a valid data record, and change the node associated with the data record to reflect the change of the memory location in the first non-volatile memory section in which memory location the data record is stored. In other words, contents of the memory location within which the data record to be changed is stored is manipulated as described for the case of deleting a data record, and the changed version of the data record is stored in the memory location of the first non-volatile memory section currently indicated by the write pointer. Subsequently, the write pointer is incremented as described above, i.e. the changed version of the data record is treated in the same manner as the other data records. Finally, the node associated with the original version of the data record is changed to be associated with the changed version of the data record. It should be noted that this approach is particularly suitable and advantageous in case the first non-volatile memory section is flash memory, since flash memory does not allow in place editing of stored information. Further, it should be noted that due to this approach, the chronological order of data records within the first non-volatile memory section, which order might have been present prior to the operation, is destroyed.

The first non-volatile memory section may be of the type that is erasable but not over-writable and that has a plurality of memory sectors that constitute the smallest erasable unit and have to be erased before being rewritten, wherein each memory sector comprises a plurality of the memory locations. In this case, it is advantageous if the storage controller is further adapted to determine prior to effecting storage of any data record whether the write pointer indicates the first memory location of a memory sector and whether this memory location is occupied, and, if the write pointer indicates the first memory location of a memory sector and if this memory location is occupied, to erase this memory sector prior to storing the data record. In a preferred embodiment, the first non-volatile memory section is flash memory.

The storage controller may further be adapted to maintain an occupation pointer that indicates the memory location among the occupied memory locations of the first non-volatile memory section for which the longest time period has elapsed since storage of the corresponding data record was effected. In this context, occupied memory locations are memory locations in which a data record is stored, regardless of whether it is valid or invalid. In order to maintain the occupation pointer, the storage controller is adapted to update the occupation pointer whenever an erasing operation on the first non-volatile memory section is performed. The occupation pointer may be utilized in order to determine when memory locations have to be erased prior to writing a new data record. This is the case whenever the write pointer and the occupation pointer indicate the same memory location.

The data management system may further comprise a second non-volatile memory section that is operably connected to the storage controller, and the storage controller may further be adapted to maintain the write pointer within the second non-volatile memory section, i.e. the write pointer information is stored within the second non-volatile memory section. In case an occupation pointer is maintained, the storage controller may further be adapted to maintain the occupation pointer within the second non-volatile memory section, i.e. the occupation pointer information is stored within the second non-volatile memory section. The second non-volatile memory section may be an electrically erasable programmable read only memory.

The storage controller may further be adapted to maintain within the volatile memory section for each linked list stored therein, at least one of a first pointer indicating the node that is associated with the data record among the data records associated with the respective linked list having the earliest time stamp, a last pointer indicating the node that is associated with the data record among the data records associated with the respective linked list having the most recent time stamp, and a last inserted pointer indicating the node that is associated with the data record among the data records associated with the respective linked list that was stored most recently into the first non-volatile memory section. These pointers may be stored within the volatile memory section and serve to facilitate management of the data records and report generation.

The data management system may further comprise a data logging means that is operably connected to the storage controller and to at least one device that is generating time stamped data during operation of the system. The data logging means may be adapted to receive data records from the at least one device and to communicate the data records to the storage controller for storage. In other words, the data logging means may simply fulfill the function of forwarding data records generated by the at least one device to the storage controller. In addition or alternatively, the data logging means may be adapted to receive data from the at least one device, to generate data records on the basis of the received data, and to communicate the data records to the storage controller for storage. In this case, the data are delivered by the at least one device e.g. in a raw format, and the data records are only generated by the data logging means. In any case, the data records communicated by the data logging means to the storage controller are the plurality of data records described above. Accordingly, the at least one device may e.g. be a sensing means within a glucose meter of a blood glucose system or a peripheral medical device of such a system, e.g. an insulin pump.

In a preferred embodiment, the data management system is included in a glucose meter of a blood glucose system, that further includes a blood glucose sensing means incorporated into the glucose meter or into a separate device. The blood glucose system preferably also further includes an insulin pump as an external device. The blood glucose sensing means, and the optional insulin pump, include a transmitter and are adapted to transmit by means of the transmitter data records to the storage controller for storage. These data records are, or in case of additional external devices form part of, the plurality of data records described above. The data records transmitted by the blood glucose sensing means include a data value characteristic of the blood glucose concentration determined during a measurement and a time stamp indicating a time at which this measurement was performed. The blood glucose sensing means and the insulin pump may be connected to the storage controller by a wired or a wireless interface. For the case that the data management system is part of a blood glucose system, the category type may be a value chosen from the group consisting of an episodic glucose concentration, a continuous glucose concentration, a basal pump rate, and a bolus amount. The system provides for a particularly fast display of records in pump history.

The volatile memory section is preferably a random access memory.

In a preferred version, the storage controller includes a microprocessor that is programmed to automatically effect one, more or all of the above-described operations of the data management system in order to effect storage of the plurality of data records.

A corresponding data management method for storing a plurality of data records including data records of at least two different category types, wherein each data record comprises a data value, an indication of the category type of the data record, and a time stamp including a time information, in a first non-volatile memory section divided into a plurality of sequentially arranged, preferably equally sized memory locations, each identified by an address and including a first memory location at one end of the first non-volatile memory section and a last memory location at the opposite end of the first non-volatile memory section, comprises the following steps: receiving the plurality of data records, determining the category type of each received data record on the basis of the indication of the category type of the respective data record, sequentially storing the data records one by one in the order they are received in the first non-volatile memory section by storing each data record into a memory location indicated by a write pointer that is incremented after each storage of a data record to indicate, in the direction from the first memory location towards the last memory location, the next memory location or, in case the last data record was stored into the last memory location, the first memory location, so that each memory location storing a data record stores exactly one data record, and for each received data record adding a new node associated with the respective data record to a linked list that is stored in a volatile memory section for the determined category type of the respective data record, such that upon storing all received data records there is a separate linked list stored in the volatile memory section for each category type included in the plurality of data records, wherein for each such linked list the nodes are only associated with data records of the same category type and the sequence of the nodes is such that the associated data records are temporally sorted according to their time stamp.

The method may further comprise the steps of determining for each data record to be stored in the first non-volatile memory section whether there is already a linked list stored in the volatile memory section for the determined category type of the respective data record, and if there is no such linked list allocating a fresh linked list and adding the new node associated with the respective data record to the fresh linked list.

The volatile memory section may comprise a plurality of sequentially arranged memory locations, each linked by a predetermined relationship to exactly one memory location of the first non-volatile memory section, and the method may further comprise the steps of adding a new node to a linked list by storing the node in the memory location of the volatile memory section that is linked by the predetermined relationship to the memory location of the first non-volatile memory section in which the data record associated with the respective node is stored.

The method may further comprise the steps of receiving an input signal indicating that a data record stored in the first non-volatile memory section is to be deleted, and deleting the data record from the first non-volatile memory section by manipulating at least one bit within the memory location of the first non-volatile memory section in which memory location the data record is stored in order to indicate that the memory location does not include a valid data record, and by removing the node associated with the data record from the corresponding linked list stored in the volatile memory section.

The method may further comprise the steps of receiving an input signal indicating that and in which manner a data record stored in the first non-volatile memory section is to be changed, storing the changed version of the data record in the memory location of the first non-volatile memory section currently indicated by the write pointer, manipulating at least one bit within the memory location of the first non-volatile memory section in which memory location the original version of the data record is stored in order to indicate that the memory location does not include a valid data record, and changing the node associated with the data record to reflect the change of the memory location in the first non-volatile memory section in which memory location the data record is stored.

The first non-volatile memory section may be of the type that is erasable but not over-writable and has a plurality of memory sectors that constitute the smallest erasable unit and have to be erased before being rewritten, wherein each memory sector comprises a plurality of the memory locations. In this case, the method may further comprise the steps of determining prior to effecting storage of any data record whether the write pointer indicates the first memory location of a memory sector and whether this memory location is occupied, and, if the write pointer indicates the first memory location of a memory sector and if this memory location is occupied, erasing this memory sector prior to storing the data record. In a preferred embodiment, the first non-volatile memory section is flash memory.

Further, an occupation pointer may be maintained that indicates the memory location among the occupied memory locations of the first non-volatile memory section for which the longest time period has elapsed since storage of the corresponding data record was effected, and that is updated whenever an erasing operation on the first non-volatile memory section is performed.

The write pointer may advantageously be maintained within a second non-volatile memory section. This second non-volatile memory section may also be used to maintain the occupation pointer. The second non-volatile memory section may be an electrically erasable programmable read only memory.

Further, for each linked list stored within the volatile memory section, at least one of a first pointer indicating the node that is associated with the data record among the data records associated with the respective linked list having the earliest time stamp, a last pointer indicating the node that is associated with the data record among the data records associated with the respective linked list having the most recent time stamp, and a last inserted pointer indicating the node that is associated with the data record among the data records associated with the respective linked list that was stored most recently into the first non-volatile memory section may be maintained within the volatile memory section.

Each linked list stored in the volatile memory section may be a doubly linked list.

The method may further comprise the steps of generating the plurality of data records at least one data generating device, transmitting the plurality of data records with the at least one data generating device, and receiving the plurality of data records for storage and/or generating data corresponding to the plurality of data records at least one data generating device, transmitting the data with the at least one data generating device, receiving the data, generating the plurality of data records on the basis of the received data, and receiving the plurality of data records for storage. In particular, the devices may be measurement devices for performing various measurements or devices having a measurement function for performing various measurements. In any case, the plurality of data records are communicated to a central component for effecting central storage.

In a preferred embodiment, the above-described method steps are performed by the components of a blood glucose system that includes a glucose meter comprising a storage controller and a blood glucose sensing means incorporated into the glucose meter or into a separate device, wherein the blood glucose sensing means includes a transmitter and the method further comprises the following steps: generating at the blood glucose sensing means data records including a data value characteristic of the blood glucose concentration determined during a measurement and a time stamp indicating a time at which this measurement was performed, and transmitting the data records as part of the plurality of data records to the storage controller for storage. The blood glucose system advantageously also comprises an insulin pump that includes a transmitter, and the method further comprises the following steps: generating at the insulin pump data records including a data value characteristic of a pump parameter and a time stamp indicating a time at which the parameter value was measured, and transmitting the data records as part of the plurality of data records to the storage controller for storage. In the case of a blood glucose system, the category type may be a value chosen from the group consisting of an episodic glucose concentration, a continuous glucose concentration, a basal pump rate, and a bolus amount.

The volatile memory section is preferably a random access memory.

Preferably, some or all of the above method steps are performed by means of a suitably programmed microprocessor or computer.

The data management method has the same advantages as described for the data management system.

In the following, the invention is explained in more detail for a preferred embodiment with reference to the figures.

FIG. 6 is a schematic diagram showing a first non-volatile memory section of the data management system of FIG. 5.

Figure 1:
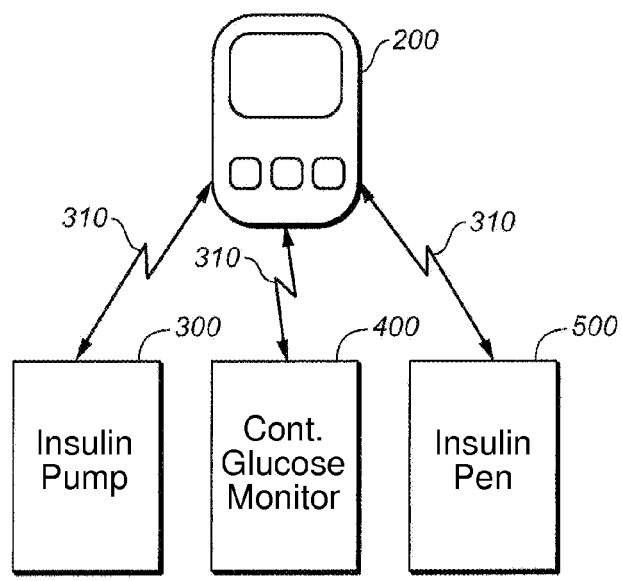
FIG. 1 shows a schematic representation of a blood glucose system including a glucose meter communicating with a plurality of peripheral medical devices using a wireless signal.

In FIG. 1 a blood glucose system is schematically shown comprising a glucose meter 200 communicating with peripheral medical devices such as, for example, an insulin pump 300, continuous glucose monitor 400, and an insulin pen 500. Both glucose meter 200 and the peripheral medical devices may send and/or receive a wireless signal 310 which can include either data or commands. Glucose meter 200 may have a need to centrally store data having different category types such as, for example, an episodic glucose measurement and a comment about the episodic glucose measurement. An exemplary embodiment of a glucose measurement device which stores several category types of data is the commercially available UltraSmart™ glucose meter from LifeScan, Inc. (Milpitas, Calif., U.S.A). There may also be a need to wirelessly transfer data for central storage from the insulin pump 300, the continuous glucose monitor 400, and/or the insulin pen 500 to the glucose meter 200 where such data may e.g. include an insulin bolus amount, an insulin bolus rate, an amount of insulin remaining in reservoir, and a time stamp. For example, storing the insulin pump data on the glucose meter 200 which also has stored glucose concentration data would allow a contemporaneous comparison between the effects of insulin therapy on the resulting glucose concentration.

Figure 2:
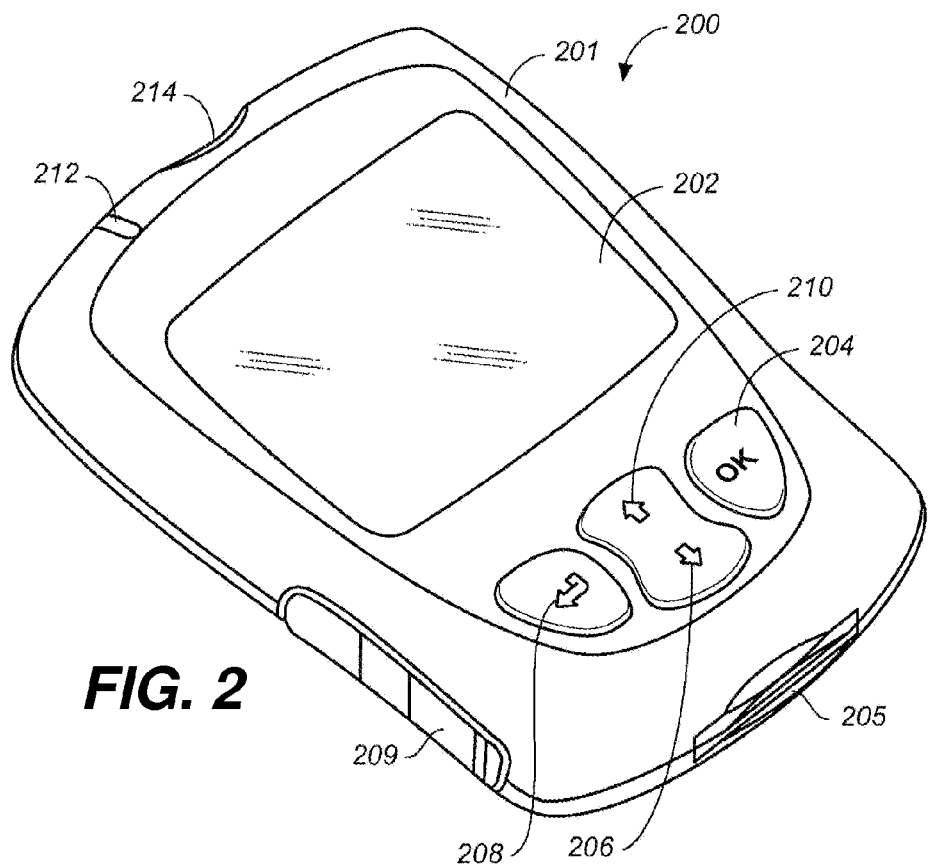
FIG. 2 is a perspective view of the glucose meter for use in the present invention.

FIG. 2 is a perspective view of a glucose meter 200 for use in the present invention. Glucose meter 200 may be used to episodically measure blood glucose and to wirelessly control insulin pump 300 and/or other peripheral medical device(s) (e.g., continuous glucose monitor 400 or insulin pen 500). In an embodiment of this invention, glucose meter 200 may be a master and insulin pump 300 and/or other peripheral medical device(s) may be a slave. Glucose meter 200 includes a housing 201, a first display 202, an OK button 204, a universal port connector 205, a down button 206, a back button 208, a port cover 209, an up button 210, light emitting diode (LED) 212, and a strip port connector (SPC) 214.

Figure 3:
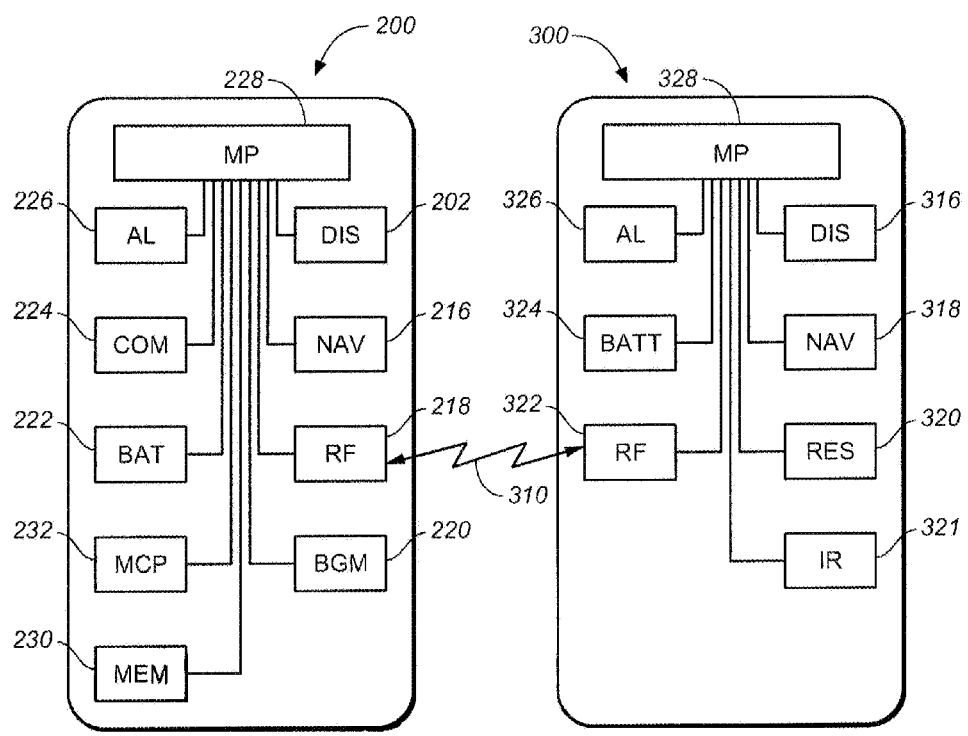
FIG. 3 is a simplified schematic view showing the functional components of the glucose meter of FIG. 2 and an insulin pump both of which are capable of wireless communication.

FIG. 3 is a simplified schematic view showing the functional components of glucose meter 200 and insulin pump 300. Glucose meter 200 includes the following functional components such as a first display (DIS) 202, a first navigational buttons (NAV) 216, a first radio frequency module (RF) 218, a blood glucose measurement (BGM) module 220, a first battery (BAT) 222, a wired communication port (COM) 224, a first alarm (AL) 226, a first microprocessor (MP) 228, a memory portion (MEM) 230 (shown in FIG. 3), and a memory chip port (MCP) 232.

First display 202 may be a liquid crystal display (LCD) to show both textual and graphical information to a user. A user interface (UI) may be a software driven menu that is shown on first display 202 that enables the user to operate glucose meter 200. A user can navigate through the UI using first navigational buttons 216 which include up button 210, down button 206, OK button 204, and back button 208, as shown in FIG. 2. In an embodiment of this invention, the UI allows a user to operate insulin pump 300, query the status of insulin pump 300, measure glucose episodically, and to display data on first display 202 from glucose meter 200 and/or insulin pump 300 and/or other peripheral medical device(s) (e.g., continuous glucose monitor 400 or insulin pen 500).

Figure 4:
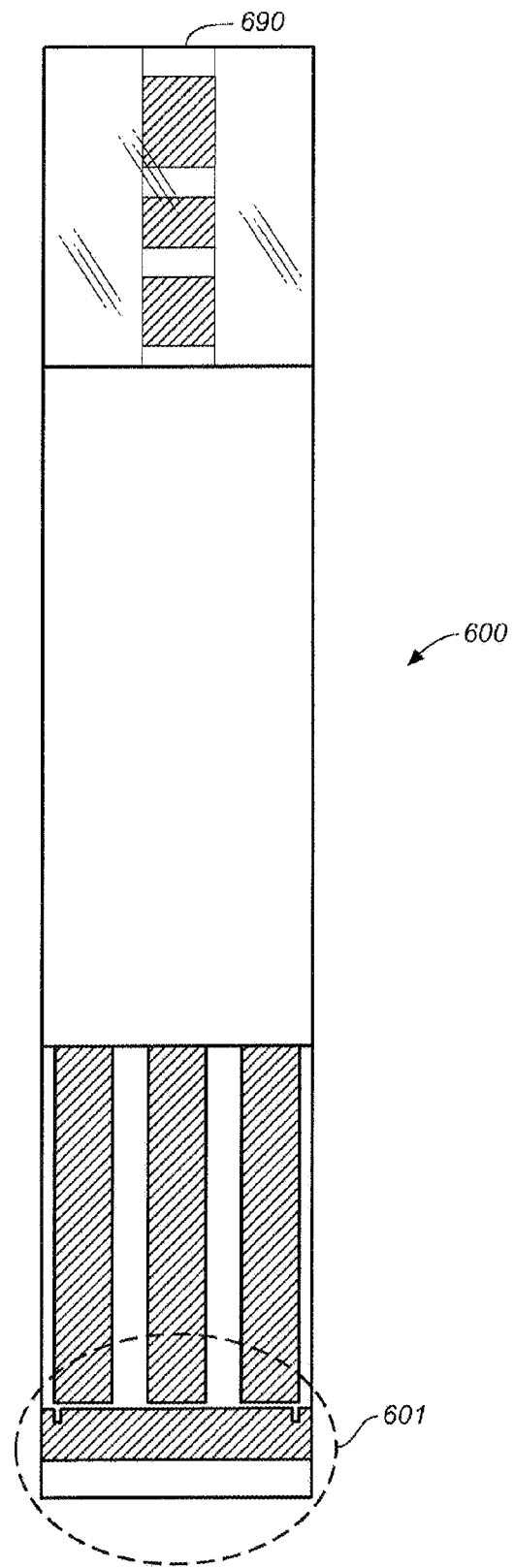
FIG. 4 is a plan view of a disposable test strip suitable for use with the glucose meter of FIG. 2.

Blood glucose measurement module 220 may be a potentiostat designed for performing an episodic electrochemical measurement of a physiological fluid. Blood glucose measurement module 220 may apply a constant potential such as, for example, about +0.4 volts (V) between a working electrode and a reference electrode of a disposable test strip. A disposable test strip 600 which may be suitable for use in the present invention is the OneTouch Ultra™ test strip which is commercially available from LifeScan, Inc. in Milpitas, Calif., U.S.A. as shown in FIG. 4. More details regarding disposable test strip 600 can be found in U.S. Pat. No. 6,733,655 which is hereby incorporated by reference herein. An electrical contact portion 601 of disposable test strip 600 may be inserted into and electrically connected with strip port connector 214 (FIG. 2). After insertion, a physiological fluid such as blood may be applied to an inlet 690 of disposable test strip 600 causing the test to initiate.

A reagent layer (not shown) on disposable test strip 600 may proportionally convert an oxidized mediator to a reduced mediator allowing a current to be measured by blood glucose measurement module 220. A portion of the current may be sampled and mathematically converted to the glucose concentration which is displayed on first display 202. Reagent layer may include chemicals such as a redox enzyme and mediator which selectivity reacts with glucose. Examples of reagent formulations or inks suitable for use in making reagent layer can be found in U.S. Pat. Nos. 5,708,247 and 6,046,051; Published International Applications WO01/67099 and WO01/73124, all of which are incorporated by reference herein.

Referring again to FIG. 3, insulin pump 300 includes the following functional components which are a second display (DIS) 316, second navigational buttons (NAV) 318, a reservoir (RES) 320, an infrared communication port (IR) 321, a second radio frequency module (RF) 322, a second battery (BAT) 324, a second alarm (AL) 326, and a second microprocessor (MP) 328. In an embodiment of this invention, insulin pump 300 and glucose meter 200 may bi-directionally communicate using a wireless signal 310 via first RF module 218 and second RF module 322.

Reservoir 320 typically contains insulin and can be dispensed out from insulin pump 300 via a tubing and needle which is attached to a user. Second navigational buttons 318 allow a user to operate and query the status of insulin pump 300.

In one aspect, a glucose meter 200 may need to store a large amount of data such as, for example, greater than about 20,000 data records. Flash memory may be used to store this large amount of data because it has several advantages such as compact size (especially compared to hard magnetic disk drives), resistance to shock, low power consumption, and relatively low cost. Memory portion 230 may be or comprise such flash memory. The glucose meter 200 may display a report or graph based on this stored data to inform the user of their general health status or effectiveness of insulin therapy. In the generation of a report or graph, the glucose meter 200 may have to query and sort a large amount of data having several different category types which may cause an undesirable delay in the report or graph generation. This problem of slow report or graph generation may be exacerbated when using flash memory because it has a relatively slow read rate compared to other forms of memory. Thus, there is a need to use an efficient data management system and method to query the data for generating a report or graph when using flash memory. Otherwise, there may be a significant delay in generating and/or scrolling through a report displayed on glucose meter 200 which is undesirable from a user's standpoint.

As one possibility for data management, flash memory may be segregated into a plurality of discrete storage areas such that each storage area is allocated for a particular category type. Each of the storage areas would be assigned to a corresponding linked list in RAM (random access memory) for maintaining the chronological order of the records. This approach has an advantage of providing easy access when displaying a report which is sorted by category type and time stamp. Additionally, this approach allows records to occupy different sizes in flash memory.

The main disadvantage of pre-defining the size allocation for each category type is that it becomes cumbersome if there is a large number of category types relative to the size of the flash memory. Further, it is difficult to predict a frequency of occurrence for a particular category type. For example, a user may have a need to store mainly episodic glucose measurement data for one month, but later has to store mainly insulin bolus data. If, for example, the glucose meter only allocated 10% of its flash memory to episodic glucose measurement data and 10% for insulin bolus data, then the user would only be able to use a relatively small fraction of the total flash memory which would be inefficient. Once a particular category type has filled its memory allocation, this would cause a need to delete a sector of that particular storage area to make room for subsequent records even though the entire flash memory is not yet full. As a result, this would prevent the full use all of the available flash memory before having to delete a sector. Note that data saved on flash memory cannot be overwritten. When the flash memory is full, an entire sector must be erased before writing to that sector again. Because of limitations of flash memory, one sector will contain more than one record, and in this invention, may be about 250 records.

In another data management scheme which is in accordance with this invention, data is serially stored on the entire capacity of the flash memory independent of the category type. This ensures that the entire flash memory is filled before having to delete a sector of the flash memory irrespective of the frequency distribution of the category types. Thus, the data records have to be stored in flash memory one after the other as they are created independent of their category type. However, this scenario has a disadvantage in that creating a report can be a slow process. For example, if the entire flash memory is full, then querying the data records for a particular category type and its time stamp can take a significant amount of time (e.g. several seconds) because in a worst case condition every record (e.g. 20,000) may have to be queried to locate a particular record.

Figure 5:
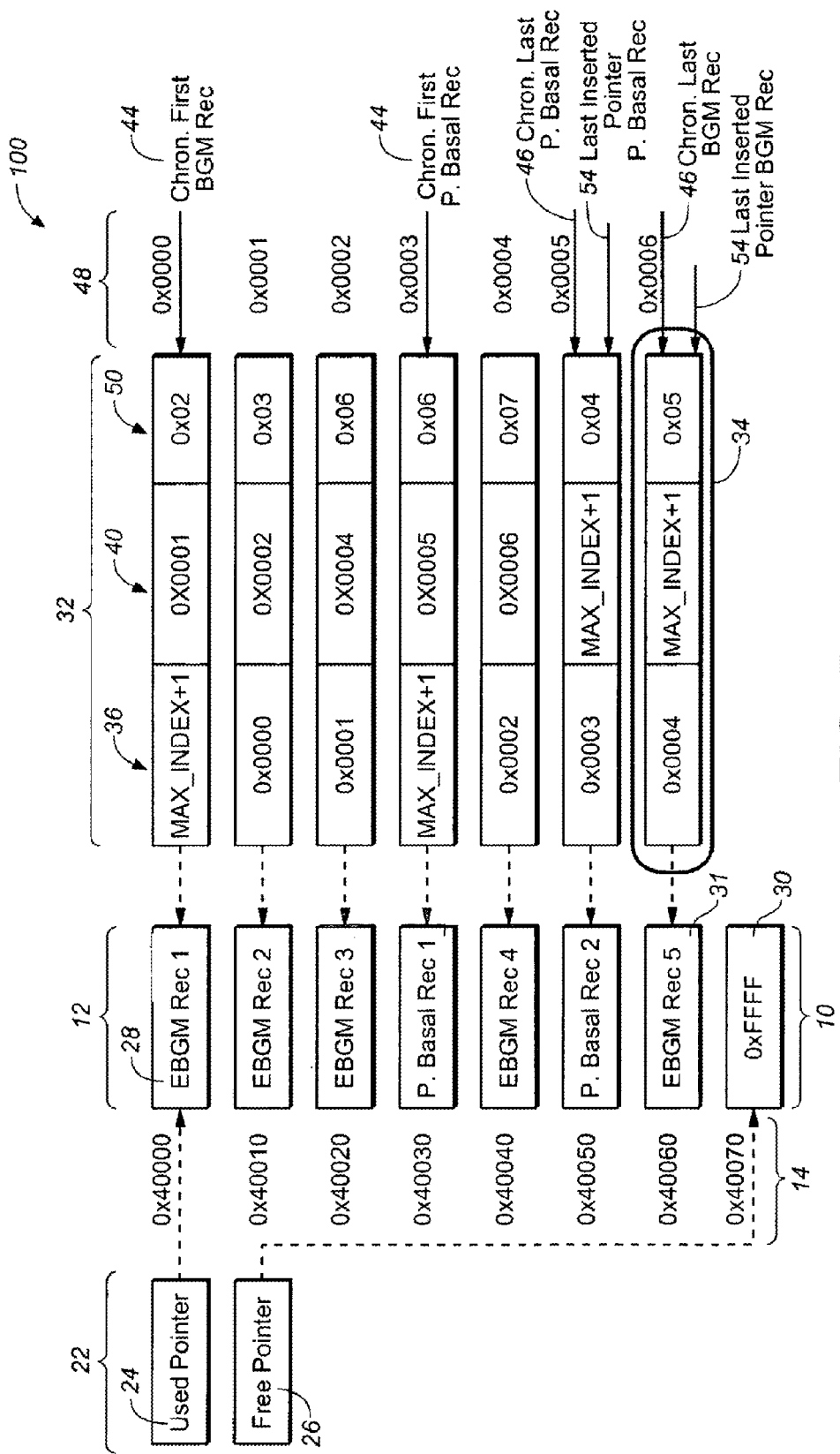
FIG. 5 is a schematic diagram showing a structure of a data management system according to an embodiment of the present invention.

In an embodiment of this invention as shown in FIG. 5, data management system 100 includes three types of memory which are a first non-volatile memory section 12, a second non-volatile memory section 22, and a volatile memory section 32. These three memory sections 12, 22, 32 may be part of memory portion 230 (shown in FIG. 3) of glucose meter 200. Data management system 100 may be used for storing a plurality of data records 10 and generating reports which include a queried sub-set of the plurality of data records 10. A data record may be used for storing data about an event. The data record may be stored in a portion of the first non-volatile memory section 12 such that each data record has the same size. As will be further described below, the three types of memory implemented into glucose meter 200 coupled with a software driven method will enable an efficient flash memory management system for fast report generation queried from a large set of data records.

FIG. 6 is an expanded schematic representation of the first non-volatile memory section 12 which shows a plurality of data records 10 stored in the first non-volatile memory section 12. Each data record 10 has a portion reserved for storing a category type 20, a data record 16, and a time stamp 21. Category type 20 may be a type of data such as, for example, an episodic blood glucose measurement (EBGM), a continuous glucose measurement, a basal pump rate (P. Basal), and a bolus amount. Data record 16 may be a number such as, for example, 60 milligrams per deciliter (mg/dL) to represent a glucose concentration or 1 unit to represent an insulin bolus amount. Data record 16 may also be in the form of text representing such as, for example, a comment about a health status of a user when performing a glucose measurement. Time stamp 21 may be a date and time in which the record was collected. Examples of other category types of data suitable of use in the present invention relate to food, medication, health, and exercise, all of which are described in U.S. Pre-Grant Publication Number U.S. 20040015102 which is hereby fully incorporated by reference herein. Examples of food related categories are a flag for noting whether the measurement was pre-prandial measurement or post-prandial, the amount of carbohydrates, fats, calories, and proteins consumed during a breakfast, lunch, dinner, or snack. Examples of medication related categories are a type of pill consumed, insulin type, insulin bolus amount, and total amount of insulin consumed for the day. Examples of a health related categories are how the user feels (hypo, ill, stressed, etc), ketone level, HbAlc level, microalbumin level, cholesterol level, and blood pressure. As can be seen, there is a need to store records in glucose meter 200 which have several different category types for helping a person with diabetes manage their disease.

In an embodiment of this invention, first non-volatile memory section 12 may be divided into a plurality of equally sized portions or memory locations for sequentially storing a plurality of records 10 as shown in FIG. 6. First non-volatile memory section 12 may be in the form of a flash memory. Each record has an address 14 indicating its location in first non-volatile memory section 12. In an embodiment of this invention, first non-volatile memory section 12 may have a capacity to store a plurality of records 10 of greater than or about 20,000. Non-volatile semiconductor memory section 12 may be organized by dividing it into a plurality of equally sized sectors of four kilobytes (4 kB) such that about 256 records may be stored in one sector. In subsequent descriptions, 256 records will be used to define a sector for exemplary purposes. The invention should not be construed as being limited to 256 records per sector. The records may be populated in a serial manner (i.e., one after the other) irrespective of the category type associated with the data record. However, as mentioned earlier, once flash memory is full, an entire sector must be deleted because flash memory does not allow overwriting.

Second non-volatile memory section 22 may be in the form of an electrically erasable programmable read only memory (EEPROM). Second non-volatile memory section 22 as shown in FIG. 5 may be used for determining which address 14 to use for writing a new record in first non-volatile memory section 12. Second non-volatile memory section 22 includes used pointer or occupation pointer 24 and a free pointer or write pointer 26. Used pointer 24 may store an address of a first record 28 written to first non-volatile memory section 12 as shown in FIG. 5. It should be noted that in the case that no erase operation was performed yet, first non-volatile memory section 12 did not contain any records before first record 28 was written. As will be evident from the following description, following each erasing operation the used pointer 24 is updated such that it stores an address of that data record stored within first non-volatile memory section 12, for which data record the longest time period has elapsed since storage, i.e. the used pointer 24 always points to the oldest data record, which is not necessarily the data record with the oldest time stamp. Free pointer 26 stores an address of an empty space 30 for writing a new record. Empty space 30 is immediately-subsequent to a last record 31 written. Once empty space 30 becomes populated with data, free pointer 26 increments to an address of an immediately-subsequent empty space 33, which in this case would be at 0x40080 as shown in FIG. 6. It should be noted that in case empty space 30 was the last memory location of first non-volatile memory section 12, so that empty space 33 is beyond first non-volatile memory section 12 or does not exist at all, incrementing the free pointer 26 involves that free pointer 26 is manipulated such that it stores an address of the first memory location, which in this case would be at 0x400000. Thus, with respect to the writing operation, the first non-volatile memory section 12 is used in the manner of a circular buffer.

Volatile memory section 32 (shown in FIG. 5) may be in the form of a random access memory (RAM). Volatile memory section 32 is used for indicating an ordinal relationship based on a time stamp for each of the records having a common category type. An index 48 refers to a location in volatile memory section 32 which in turn links to a location in first non-volatile memory section 12 as shown in FIG. 5. Volatile memory section 32 stores a linked information set 34 for each of the records stored in first non-volatile memory section 12.

For each record, linked information set 34 includes an immediately-previous record index 36, an immediately-subsequent record index 40, and a checksum 50. For a particular record, immediately-previous record index 36 stores an index indicating the location of the information set 34 linked to the record having the next earlier time stamp and having the same category type as the particular record. However, if the record linked to the information set 34 is the record for a particular category type having the earliest time stamp, then there is not an applicable index of an information set 34 linked to an immediately-previous record. In such a case, the immediately-previous record index 36 may be populated with the designation or value "MAX_INDEX+1" as shown in FIG. 5.

For a particular record, immediately-subsequent record index 40 stores an index indicating the location of the information set 34 linked to the record having the next later time stamp and having the same category type as the particular record. However, if the record linked to the information set 34 is the record for a particular category type having the most recent time stamp, then there is not an applicable index of an information set 34 linked to an immediately-subsequent record. In such a case, the particular immediately-subsequent record index 40 may be populated with the designation or value "MAX_INDEX+1" as shown in FIG. 5.

Thus, a plurality of linked information sets 34 having the same category type will provide the information needed to locate all of the relevant records in first non-volatile memory section 12. All information sets 34 linked to data records of the same category type together form a linked list with the information sets 34 being the nodes of the linked list.

Linked information set 34 further includes a first pointer 44 and a last pointer 46 for each category type as shown in FIG. 5. Pointers 44 and 46 may be stored in each of the information sets 34 or may be stored in volatile memory section 32 in addition to the plurality of information sets 34. First pointer 44 and last pointer 46 may be used for reading the records such that they can be found quickly. For a particular category type, first pointer 44 includes an index for the information set 34 linked to a chronological first record (i.e., a record with the earliest time stamp) as shown in FIG. 5. In an embodiment of this invention, all entries under immediately-previous record index 36 denoted as "MAX_INDEX+1" may correspond to an index for first pointer 44 for a particular category type. For a particular category type, last pointer 46 includes an index for the information set 34 linked to a chronological last record (record with the most recent time stamp) as shown in FIG. 5. In an embodiment of this invention, all entries under immediately-subsequent record index 40 denoted as "MAX_INDEX+1" may correspond to an index for last pointer 46 for a particular category type.

Linked information set 34 yet further includes a last inserted pointer 54 for each category type as shown in FIG. 5. Pointer 54 may be stored in each of the information sets 34 or may be stored in volatile memory section 32 in addition to the plurality of information sets 34. Last inserted pointer 54 may be used to find quickly the insertion point in the double linked list of the volatile memory section 32. For a particular category type, last inserted pointer 54 includes an index of the information set 34 linked to the last stored or inserted record independent of its time stamp. In FIG. 5, last pointer 46 and last inserted pointer 54 have the same index. However, when a record is edited, last pointer 46 and last inserted pointer 54 will have a different index as will be described in a subsequent section.

In routine use, glucose meter 200 will continually store new records as a user tests his or her glucose level and/or operates insulin pump 300 until first non-volatile memory section 12 becomes full (e.g., all 20,000 records have been stored). When this occurs, data management system 100 must determine which record or records must be deleted or overwritten so that a new record can be stored. However if first non-volatile memory section 12 is flash memory, single records cannot be deleted to make room for a new record that needs to be stored. For flash memory, an entire sector must be deleted which may be, for example, 256 records.

The first sector to be deleted after completely filling up the first non-volatile memory section 12 for the first time may be the 256 records starting at the address stored in free pointer 26. In this case, free pointer 26 will be pointing to the first record in first non-volatile memory section 12. Thus, the 256 records will have to be from the beginning of first non-volatile memory section 12 at used pointer 24. For example, after the first non-volatile memory section 12 become full for the first time, the records corresponding to addresses 0x40000 to 0x40FFF (not shown) will be deleted. After deleting the first sector, used pointer 24 is set to the beginning of the second sector which is at address 0x41000 (not shown), i.e. to the data record for which at that moment the longest time period has elapsed since storage of the corresponding data record was effected. It should be noted that the first sector has to be deleted once free pointer 26 points to the same address as used pointer 24.

Once the first sector is filled with 256 records, which is the case once free pointer 26 again points to the same address as used pointer 24 at the beginning of the second sector, the second sector must be deleted which is defined as the 256 records stored beginning at the address stored in free pointer 26 which in this case would be 0x41000 (not shown). After deleting the second sector, used pointer 24 is set to the beginning of the third sector which is at address 0x42000 (not shown), i.e. again to the data record for which at that moment the longest time period has elapsed since storage of the corresponding data record was effected. It should be noted that similar to the situation in which the first sector had to be deleted the second sector has to be deleted once free pointer 26 points to the same address as used pointer 24. Subsequent sectors are then deleted whenever free pointer 26 points to the same address as used pointer 24 in a similar manner where 256 records are deleted at a time.

Under certain circumstances, a user may want to delete one or more of the records stored in the first non-volatile memory section 12. For example, a user may want to delete a record that was a practice episodic glucose measurement. For these type of cases the record to be deleted is marked with a flag, e.g. by manipulating one or more predetermined bits within the memory location storing this record. The record is not actually deleted and thus can be read as "raw data" under certain circumstances. However, a record marked with a flag is not included in reports or queries of first non-volatile memory section 12. A record marked with a flag is eventually deleted when the sector that the record is stored in is deleted.

Figure 7:
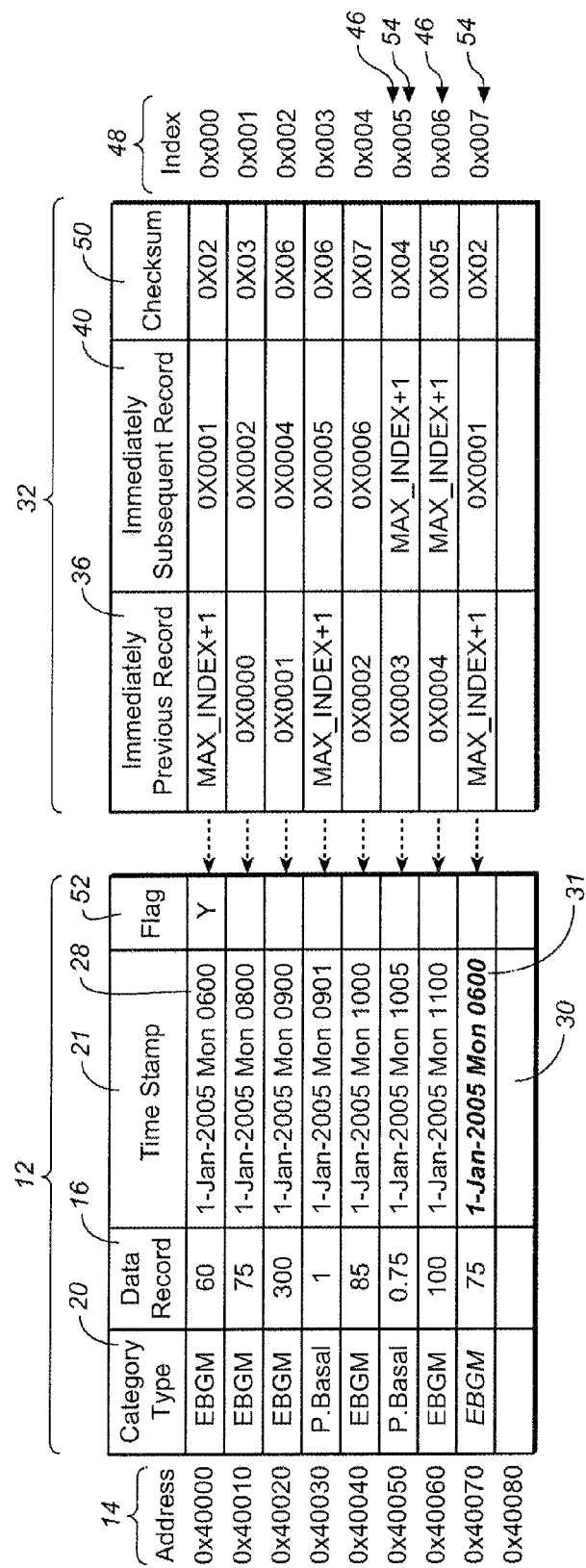
FIG. 7 is a schematic diagram showing an addition of a data record on the first non-volatile memory section and the positioning of a last pointer (based on most recent time stamp) and a last inserted pointer (based on most recently written to memory).

In other instances, a user may want to edit a record. For example, as shown in FIG. 7, a user may change a value such as a glucose concentration from 60 to 75 for a record at the address 0x40000. When the record is edited as shown in FIG. 7, it is marked with a flag 52, formed e.g. by one or more predetermined bits within the memory location at the address 0x40000, and then the modified record is written to first non-volatile memory section 12 having an address indicated by free pointer 26 in the same manner as described above for a new record (see FIG. 5). Editing a record time shifts the modified record to a future time period because the initial record is rewritten to a subsequent or down stream portion of first non-volatile memory section 12 which in this case is at 0x40070. It should be noted that the plurality of records 10 are not necessarily stored in the order they were received when an edit is made to one of the records. Further, it should be noted that in general the plurality of records 10 are not necessarily stored in chronological order by time stamp, because the data records may e.g. be received in batches from different external devices, where each external device transmits such a batch from time to time only. However, even if the plurality of data records would initially have been stored in chronological order by time stamp, this chronological order would likely be destroyed when an edit is made to one of the records. For example, in FIG. 7, the record stored in first non-volatile memory section 12 at the address 0x40000 has the earliest time stamp 21, but after editing, the record is now stored at the address 0x40070 which is the last written record. By editing the oldest record based on time stamp, the record has been shifted downstream and possibly to another sector within first non-volatile memory section 12. Therefore, it is possible that the oldest records with the earliest time stamp may not always be deleted when deleting a sector.

The glucose meter 200 is adapted to generate and display a report which may include a listing of records having a common category type and be listed in chronological order according to a time stamp associated with each of the records. In an embodiment of this invention, linked information set 34 allows for fast generation of such a report such that there is no delay in scrolling through the report. It is an advantage of this invention that the use of second non-volatile memory section 22 and volatile memory section 32 allows a plurality of records 10 stored in first non-volatile memory section 12 to be displayed as a report organized by category type and by time stamp more quickly than if only the first non-volatile memory section 12 were to be used. Examples of such reports may be a glucose log book or an insulin pump history on an LCD display.

The glucose meter 200 may be adapted to perform the above described functions and operations by means of the microprocessor 228 being suitably programmed. In other words, microprocessor 228 is suitably programmed such that it is operable to semi-automatically or preferably automatically control the glucose meter 200 such that it performs some or all of the above described functions and operations.

The invention claimed is:

1. A data management system comprising:
   a first non-volatile memory section divided into a plurality of sequentially arranged memory locations, each identified by an address and including a first memory location at one end of the first non-volatile memory section and a last memory location at the opposite end thereof,
   a volatile memory section, and
   a storage controller operably connected to the first non-volatile memory section and the volatile memory section and adapted to:
   receive a plurality of data records including data records of at least two different category types, wherein each data record comprises a data value, an indication of the category type of the respective data record, and a time stamp including a time information,
   determine the category type of each received data record on the basis of the indication of the category type of the respective data record,
   sequentially store one by one the data records in the order they are received in the first non-volatile memory section by storing each data record into a memory location indicated by a write pointer that is maintained by the storage controller and that is incremented after each storage of a data record to indicate, in the direction from the first memory location towards the last memory location, the next memory location or, in case the last data record was stored into the last memory location, the first memory location, so that each memory location storing a data record stores exactly one data record, and
   for each received data record, add a new node associated with the received data record to a linked list that is stored in the volatile memory section for the determined category type of the received data record, such that upon storing all received data records there is a separate linked list stored in the volatile memory section for each category type included in the plurality of data records, wherein for each such linked list the nodes are only associated with data records of the same category type and the sequence of the nodes is such that the associated data records are temporally sorted according to their time stamp.

2. The data management system according to claim 1, wherein the storage controller is adapted to determine for each data record to be stored in the first non-volatile memory section whether there is already a linked list stored in the volatile memory section for the determined category type of the data record to be stored, and if there is no such linked list, to allocate a fresh linked list and to add a new node associated with the data record to be stored to the fresh linked list.

3. The data management system according to claim 1, wherein the volatile memory section comprises a plurality of sequentially arranged memory locations, each linked by a predetermined relationship stored in the storage controller to exactly one memory location of the first non-volatile memory section, wherein the storage controller is adapted to add a new node to a linked list by storing the node in the memory location of the volatile memory section that is linked by the predetermined relationship to the memory location of the first non-volatile memory section in which the data record associated with the respective node is stored.

4. The data management system according to claim 1, wherein the storage controller is adapted to receive an input signal indicating that a data record stored in the first non-volatile memory section is to be deleted, and is adapted to delete the data record from the first non-volatile memory section by manipulating at least one bit within the memory location of the first non-volatile memory section in which memory location the data record is stored in order to indicate that the memory location does not include a valid data record, and by removing the node associated with the data record from the corresponding linked list stored in the volatile memory section.

5. The data management system according to claim 1, wherein the storage controller is adapted to receive an input signal indicating that, and in which manner, a data record stored in the first non-volatile memory section is to be changed, and is adapted to store the changed data record in the memory location of the first non-volatile memory section currently indicated by the write pointer, to manipulate at least one bit within the memory location of the first non-volatile memory section in which memory location the data record is stored in order to indicate that the memory location does not include a valid data record, and to change the node associated with the data record to reflect the change of the memory location in the first non-volatile memory section in which memory location the data record is stored.

6. The data management system according to claim 1, further adapted to maintain within the volatile memory section for each linked list stored therein, at least one of a first pointer indicating the node, associated with the data record among the data records associated with the respective linked list, having the earliest time stamp, a last pointer indicating the node, associated with the data record among the data records associated with the respective linked list, having the most recent time stamp, and a last inserted pointer indicating the node, associated with the data record among the data records associated with the respective linked list, that was stored most recently into the first non-volatile memory section.

7. The data management system according to claim 1, wherein the plurality of sequentially arranged memory locations, into which the first non-volatile memory section is divided, are equally sized.

8. The data management system according to claim 1, wherein the volatile memory section comprises a random access memory.

9. The data management system according to claim 1, wherein the storage controller includes a microprocessor that is programmed to automatically effect the operations of the data management system in order to effect storage of the plurality of data records.

10. The data management system according to claim 1, wherein each linked list stored in the volatile memory section is a doubly linked list.

11. The data management system according to claim 10, wherein the data management system is included in a blood glucose system comprising an insulin pump having a transmitter adapted to transmit by means of the transmitter data records of the insulin pump to the storage controller for storage in the data management system.

12. The data management system according to claim 10, wherein the category type comprises a value chosen from the group consisting of an episodic glucose concentration, a continuous glucose concentration, a basal pump rate, and a bolus amount.

13. The data management system according to claim 1, wherein the first non-volatile memory section is erasable but not over-writable and has a plurality of memory sectors, and wherein a sector constitutes the smallest erasable unit and has to be erased before being rewritten, wherein each memory sector comprises a plurality of the memory locations.

14. The data management system according to claim 13, wherein the first non-volatile memory section comprises a flash memory.

15. The data management system according to claim 13, wherein the storage controller is further adapted to determine prior to effecting storage of any data record whether a write pointer indicates the first memory location of a memory sector and whether this memory location is occupied, and, if the write pointer indicates the first memory location of a memory sector and if this memory location is occupied, to erase this memory sector prior to storing the data record.

16. The data management system according to claim 15, wherein the storage controller is further adapted to maintain an occupation pointer that indicates the memory location among the occupied memory locations of the first non-volatile memory section for which the longest time period has elapsed since storage of the corresponding data record was effected, and adapted to update the occupation pointer whenever an erasing operation on the first non-volatile memory section is performed.

17. The data management system according to claim 16, further comprising a second non-volatile memory section operably connected to the storage controller, wherein the storage controller is adapted to maintain the write pointer within the second non-volatile memory section.

18. The data management system according to claim 17, wherein the storage controller is adapted to maintain an occupation pointer within the second non-volatile memory section.

19. The data management system according to claim 17, wherein said second non-volatile memory section comprises an electrically erasable programmable read only memory.

20. A data management method for storing a plurality of data records including data records of at least two different category types, wherein each data record comprises a data value, an indication of the category type of the respective data record, and a time stamp including a time information, in a first non-volatile memory section divided into a plurality of sequentially arranged memory locations, each identified by an address and including a first memory location at one end of the first non-volatile memory section and a last memory location at the opposite end of the first non-volatile memory section, the method comprising the following steps:
receiving the plurality of data records,
determining the category type of each received data record on the basis of the indication of the category type of the respective data record,
sequentially storing the data records one by one in the order they are received in the first non-volatile memory section by storing each data record into a memory location indicated by a write pointer that is incremented after each storage of a data record to indicate, in the direction from the first memory location towards the last memory location, the next memory location or, in case the last data record was stored into the last memory location, the first memory location, so that each memory location storing a data record stores exactly one data record, and
for each received data record, adding a new node associated with the respective data record to a linked list that is stored in a volatile memory section for the determined category type of the respective data record, such that upon storing all received data records there is a separate linked list stored in the volatile memory section for each category type included in the plurality of data records, wherein for each such linked list the nodes are only associated with data records of the same category type and the sequence of the nodes is such that the associated data records are temporally sorted according to their time stamp.

21. The method according to claim 20, further comprising the steps of determining for each data record to be stored in the first non-volatile memory section whether there is already a linked list stored in the volatile memory section for the determined category type of the data record to be stored, and if there is no such linked list, allocating a fresh linked list and adding a new node associated with the data record to be stored to the fresh linked list.

22. The method according to claim 20, wherein the volatile memory section comprises a plurality of sequentially arranged memory locations, each linked by a predetermined relationship to exactly one memory location of the first non-volatile memory section, wherein the method further comprises the steps of adding a new node to a linked list by storing the node in the memory location of the volatile memory section that is linked by the predetermined relationship to the memory location of the first non-volatile memory section in which the data record associated with the respective node is stored.

23. The method according to claim 20, further comprising the steps of
receiving an input signal indicating that a data record stored in the first non-volatile memory section is to be deleted, and
deleting the data record from the first non-volatile memory section by manipulating at least one bit within the memory location of the first non-volatile memory section in which memory location the data record is stored in order to indicate that the memory location does not include a valid data record, and by removing the node associated with the data record from the corresponding linked list stored in the volatile memory section.

24. The method according to claim 20, further comprising the steps of
receiving an input signal indicating that, and in which manner, a data record stored in the first non-volatile memory section is to be changed,
storing the changed data record in the memory location of the first non-volatile memory section currently indicated by the write pointer,
manipulating at least one bit within the memory location of the first non-volatile memory section in which memory location the data record is stored in order to indicate that the memory location does not include a valid data record, and changing the node associated with the data record to reflect the change of the memory location in the first non-volatile memory section in which memory location the data record is stored.

25. The method according to claim 20, wherein the volatile memory section comprises a random access memory.

26. The method according to claim 20, wherein some or all of the method steps are performed by a suitably programmed computer.

27. The method according to claim 20, wherein the first non-volatile memory section is erasable but not over-writable and has a plurality of memory sectors, wherein a sector constitutes the smallest erasable unit and has to be erased before being rewritten, and wherein each memory sector comprises a plurality of the memory locations.

28. The method according to claim 27, wherein the first non-volatile memory section comprises a flash memory.

29. The method according to claim 27, further comprising the steps of determining prior to effecting storage of any data record whether the write pointer indicates the first memory location of a memory sector and whether this memory location is occupied; and, if the write pointer indicates the first memory location of a memory sector and if this memory location is occupied, erasing this memory sector prior to storing the data record.

30. The method according to claim 29, wherein an occupation pointer is maintained that indicates the memory location among the occupied memory locations of the first non-volatile memory section for which the longest time period has elapsed since storage of the corresponding data record was effected, and that is updated whenever an erasing operation on the first non-volatile memory section is performed.

31. The method according to claim 30, wherein the write pointer is maintained within a second non-volatile memory section.

32. The method according to claim 31, wherein the occupation pointer is maintained within the second non-volatile memory section.

33. The method according to claim 31, wherein the second non-volatile memory section comprises an electrically erasable programmable read only memory.

34. The method according to claim 33, wherein for each linked list stored within the volatile memory section, at least one of a first pointer indicating the node, associated with the data record among the data records associated with the respective linked list, having the earliest time stamp, and a last pointer indicating the node, associated with the data record among the data records associated with the respective linked list, having the most recent time stamp, and a last inserted pointer indicating the node, associated with the data record among the data records associated with the respective linked list, that was stored most recently into the first non-volatile memory section, is maintained within the volatile memory section.

35. The method according to claim 34, wherein each linked list stored in the volatile memory section is a doubly linked list.

36. The method according to claim 20, further comprising the following steps:
generating the plurality of data records from at least one data generating device, wherein the at least one data generating device comprises one of an insulin pump and glucose meter that includes a transmitter and a storage controller, the storage controller operably connected to the first nonvolatile memory section and the volatile memory section, for storage of data records from said one of the insulin pump and glucose meter,
transmitting the plurality of data records with the at least one data generating device, and receiving the plurality of data records for storage,
generating data corresponding to the plurality of data records at the at least one data generating device, and
transmitting the data with the at least one data generating device, receiving the data, generating the plurality of data records on the basis of the received data, and receiving the plurality of data records for storage.

37. The method according to claim 36, wherein the method further comprises the following steps:
generating data records including a data value characteristic of a pump parameter and a time stamp indicating a time at which the data value characteristic of the pump parameter was measured, and
transmitting the data records as part of the plurality of data records to the storage controller for storage.

38. The method according to claim 37, wherein the category type comprises a value chosen from the group consisting of an episodic glucose concentration, a continuous glucose concentration, a basal pump rate, and a bolus amount.

39. The method according to claim 38, wherein the plurality of sequentially arranged memory locations, into which the first non-volatile memory section is divided, are equally sized.

* * * * *